US012729364B2

(12) United States Patent
Bielawski et al.

(10) Patent No.: US 12,729,364 B2
(45) Date of Patent: Sep. 8, 2026

(54) OPTICAL MEASUREMENT OF BIOLOGICAL TISSUE

(71) Applicant: OPTICS11 B.V., Amsterdam (NL)

(72) Inventors: Kevin Bielawski, Amsterdam (NL); Niek Rijnveld, Amsterdam (NL); Grzegorz Gruca, Amsterdam (NL); Ramkumar Raghuraman, Amsterdam (NL); Jakob Pyszkowski, Amsterdam (NL); Matthias Haalstra, Amsterdam (NL); Kyle Juedes, Amsterdam (NL)

(73) Assignee: OPTICS11 B.V., Amsterdam (NL)

( * ) Notice: Subject to any disclaimer, the term of this patent is extended or adjusted under 35 U.S.C. 154(b) by 366 days.

(21) Appl. No.: 18/684,786

(22) PCT Filed: Aug. 19, 2022

(86) PCT No.: PCT/NL2022/050477
§ 371 (c)(1),
(2) Date: Feb. 19, 2024

(87) PCT Pub. No.: WO2023/022597
PCT Pub. Date: Feb. 23, 2023

(65) Prior Publication Data

US 2024/0425798 A1 Dec. 26, 2024

(30) Foreign Application Priority Data

Aug. 19, 2021 (NL) ..................................... 2029002

(51) Int. Cl.
*C12M 1/34* (2006.01)
*C12M 1/36* (2006.01)
(Continued)

(52) U.S. Cl.
CPC ............ *C12M 41/46* (2013.01); *C12M 21/08* (2013.01); *C12M 35/02* (2013.01); *C12M 35/04* (2013.01);
(Continued)

(58) Field of Classification Search
CPC ...... C12M 41/46; C12M 21/08; C12M 35/02; C12M 35/04; C12M 41/48; C12M 23/48;
(Continued)

(56) References Cited

U.S. PATENT DOCUMENTS 5,891,747 A * 4/1999 Farah ..................... G01H 9/004 356/482
6,289,717 B1 * 9/2001 Thundat ........... G01N 33/54373 436/163
(Continued)

FOREIGN PATENT DOCUMENTS

CN 110231468 A * 9/2019 ............. G01D 5/268
FR 3032201 A1 8/2016
(Continued)

OTHER PUBLICATIONS

Alunda, B. O., & Lee, Y. J. (2020). Review: Cantilever-Based Sensors for High Speed Atomic Force Microscopy. Sensors, 20(17), 4784. https://doi.org/10.3390/s20174784 (Year: 2020).*
(Continued)

*Primary Examiner* — Tarifur R Chowdhury
*Assistant Examiner* — Kaitlyn E Kidwell
(74) *Attorney, Agent, or Firm* — KARCESKI IP LAW, PLLC

(57) ABSTRACT

An optical measurement assembly includes a tissue suspension device having two cantilevers between which a biological tissue can be suspended. This assembly further an optical waveguide having an end that faces a surface part of one of the two cantilevers. The surface part is optically
(Continued)

reflective so that the optical waveguide and the surface part form an interferometric cavity. This interferometric cavity has a spectral response that varies as a function of a degree of flexion of the cantilever of which the surface part faces the optical waveguide.

19 Claims, 3 Drawing Sheets

(51) Int. Cl.
*C12M 1/42* (2006.01)
*C12M 3/00* (2006.01)
*G01D 5/353* (2006.01)

(52) U.S. Cl.
CPC ......... *C12M 41/48* (2013.01); *G01D 5/35306* (2013.01)

(58) Field of Classification Search
CPC ............ G01D 5/35306; G01D 5/35312; G01L 1/242; G01L 1/245; G01L 9/0079; G01L 1/00; G01B 11/161; G01B 9/02027; G01J 3/0218; G01J 3/26; G01N 2291/0255; G01N 33/4833; G01N 33/483; G01N 33/54373
See application file for complete search history.

(56) References Cited

U.S. PATENT DOCUMENTS

2014/0141525 A1* 5/2014 Albert .............. G01N 33/54373 422/69
2017/0260488 A1 9/2017 Costa et al.
2024/0295395 A1* 9/2024 Rijnveld ............ G01D 5/35312

FOREIGN PATENT DOCUMENTS

WO 2017077138 A1 5/2017
WO 2021112666 A1 6/2021

OTHER PUBLICATIONS

International Search Report and Written Opinion dated Nov. 18, 2022, for International Patent Application No. PCT/NL2022/050477.

* cited by examiner

OPTICAL MEASUREMENT OF BIOLOGICAL TISSUE

CROSS-REFERENCE TO RELATED APPLICATION(S)

This is a National Stage Entry into the United States Patent and Trademark Office from International Patent Application No. PCT/NL2022/050477, filed on Aug. 19, 2022, which relies on and claims priority to Netherlands Patent Application No. 2029002, filed on Aug. 19, 2021, the entire contents of both of which are incorporated herein by reference.

FIELD OF THE INVENTION

An aspect of the invention relates to an optical measurement assembly for measuring a functional property of biological tissue. The biological tissue may be, for example, an engineered biological tissue that has been grown in an incubator. A functional property to be measured may concern, for example, a force that the biological tissue is able to generate in response to an electrical stimulus. Other aspects of the invention relate to a complex of optical measurement assemblies, an optical measurement system, and a method of optically measuring at least one functional property of a biological tissue.

BACKGROUND OF THE INVENTION

Measurement of functional properties of biological tissues has emerged as a promising method to non-destructively and quickly assess quality and health of these tissues. One functional property of importance concerns a force that a biological tissue is able to generate in response to an electrical stimulus. By monitoring the force in combination with the electrical stimulus, relevant information on the biological tissue can be obtained. This information may pertain to, for example, a degree of maturity of the biological tissue, an effect of a drug on arrythmias, and a general response to a drug. This information is typically gathered in two-dimensional assays. However, these may not sufficiently well mimic an adult tissue. Using a three-dimensional bundle of tissue allows obtaining more relevant information about the biological tissue.

Patent publication US20170260488 describes a bioreactor system that can measure one or more properties of engineered tissue. In the bioreactor system, two posts are suspended in the culture well: a flexible post and a rigid post. Engineered tissue is grown between these two posts. A contractile force of the engineered tissue is measured as follows. The flexible post comprises an optical fiber that is operatively coupled to a light source. A position sensitive detector, which is disposed below a transparent floor of the culture well, detects movement of the flexible post. The flexible post thus serves as both a light guide to the position sensitive detector as well as a cantilever for measuring tissue contractions. The position-sensitive detector is an optical position sensor that can measure a position of a light spot in one or two-dimensions on a sensor surface. Specifically, the position-sensitive detector utilizes photodiode surface resistance to determine the position (location) of the light spot. The position-sensitive photodetector, which is beneath a free end of the optical fiber, receives light transmitted through the optical fiber and detects the displacement of the free end of the optical fiber. This photodetector signal is recorded and converted to a displacement and a tissue-generated force based on an equation for a bending cantilever beam.

SUMMARY OF THE INVENTION

There is a need for a technique for measuring a functional property of biological tissue that allows an improvement in at least one of the following aspects: precision, versatility, and ease-of-use.

An aspect of the invention as defined in claim 1 provides for optical measurement assembly comprising:

- a tissue suspension device having two cantilevers between which a biological tissue can be suspended; and
- an optical waveguide having an end that faces a surface part of one of the two cantilevers, the surface part being optically reflective so that the optical waveguide and the surface part form an interferometric cavity having a spectral response that varies as a function of a degree of flexion of the cantilever of which the surface part faces the optical waveguide.

A further aspect of the invention as defined in claim 10 provides for a complex of optical measurement assemblies as defined hereinbefore, wherein respective interferometric cavities have respective spectral responses that are different from each other.

Yet a further aspect of the invention as defined in claim 12 provides for an optical measurement system comprising an optical measurement assembly as defined hereinbefore, and an optical interrogator adapted to measure a change in the spectral response of the interferometric cavity formed by the end of the optical waveguide and the surface part of the cantilever that faces the end of the optical waveguide.

Yet further aspects of the invention as defined in claims 15 and 16 provide for use of an optical measurement assembly as defined hereinbefore for measuring at least one functional property of biological tissue, and a method of optically measuring at least one functional property of a biological tissue, the method comprising:

- providing a biological tissue that is suspended between two cantilevers of a tissue suspension device;
- positioning the tissue suspension device with respect to an end of an optical waveguide so that the end of the optical waveguide faces a surface part of one of the two cantilevers, the surface part being optically reflective so that the end of the optical waveguide and the surface part form an interferometric cavity having a spectral response that varies as a function of a degree of flexion of the cantilever of which the surface part faces the optical waveguide;
- measuring a change in the spectral response of the interferometric cavity; and
- calculating a force exerted by the biological tissue on the basis of the change in the spectral response of the interferometric cavity, the force being representative of a functional property of the biological tissue.

In each of these aspects, the invention allows a significantly higher precision and sensitivity with which a functional property of the tissue can be measured compared with the prior-art technique described hereinbefore. Namely, the change in the spectral response of the optical interferometric cavity can be measured with a relatively high degree of precision and accuracy. The change in the spectral response can be precisely related to a force that the biological tissue exerts on the two cantilevers and, more generally to a functional property of the biological tissue. What is more, even a relatively small change in the spectral response can be measured, which means that a relatively weak force exerted by the biological tissue can be measured. The invention allows measurements with a degree of precision and sensitivity that can be several orders of magnitude higher than what is achievable with prior-art techniques.

The relatively high degree of precision and sensitivity that can be achieved thanks to the invention can provide various advantages in growing and analyzing biological tissues. For example, compared with prior-art techniques, sufficiently reliable measurements can be carried out on less mature biological tissues, which are weaker. In turn, this allows higher throughput in laboratories and other environments where biological tissues are grown and analyzed. Further, the invention allows embodiments in which multiple biological tissues can be analyzed simultaneously, which also contributes to achieving a relatively high throughput.

Another advantage is as follows. Relatively small differences and variations in environmental conditions generally have weak effects on biological tissues. The invention allows measuring these weak effects in a sufficiently reliable manner. A stimulus-response relationship that a biological tissue exhibits can be monitored in real time. In such monitoring, the invention allows higher time resolution compared with conventional video imaging methods.

In addition, embodiments of the invention may be based on standard incubators without making significant changes to these incubators. There is a high degree of compatibility. The invention also provides compatibility with fluorescence imaging. A measurement in accordance with the invention, which is of an optical nature, can be carried out in combination with screening of a fluorescent marker.

Incubator-based embodiments of the invention allow making measurements in a precise and reliable manner, continually throughout a duration of an experiment. In contrast, solutions that involve incorporating sensitive electronic devices in an incubator, are less compatible. Moreover, these conventional solutions may be less performant in making long-term continuous measurements.

For the purpose of illustration, some embodiments of the invention are described in detail with reference to accompanying drawings. In this description, additional features will be presented, some of which are defined in the dependent claims, and advantages will be apparent.

DESCRIPTION OF EMBODIMENT(S) OF THE INVENTION

Figure 1:
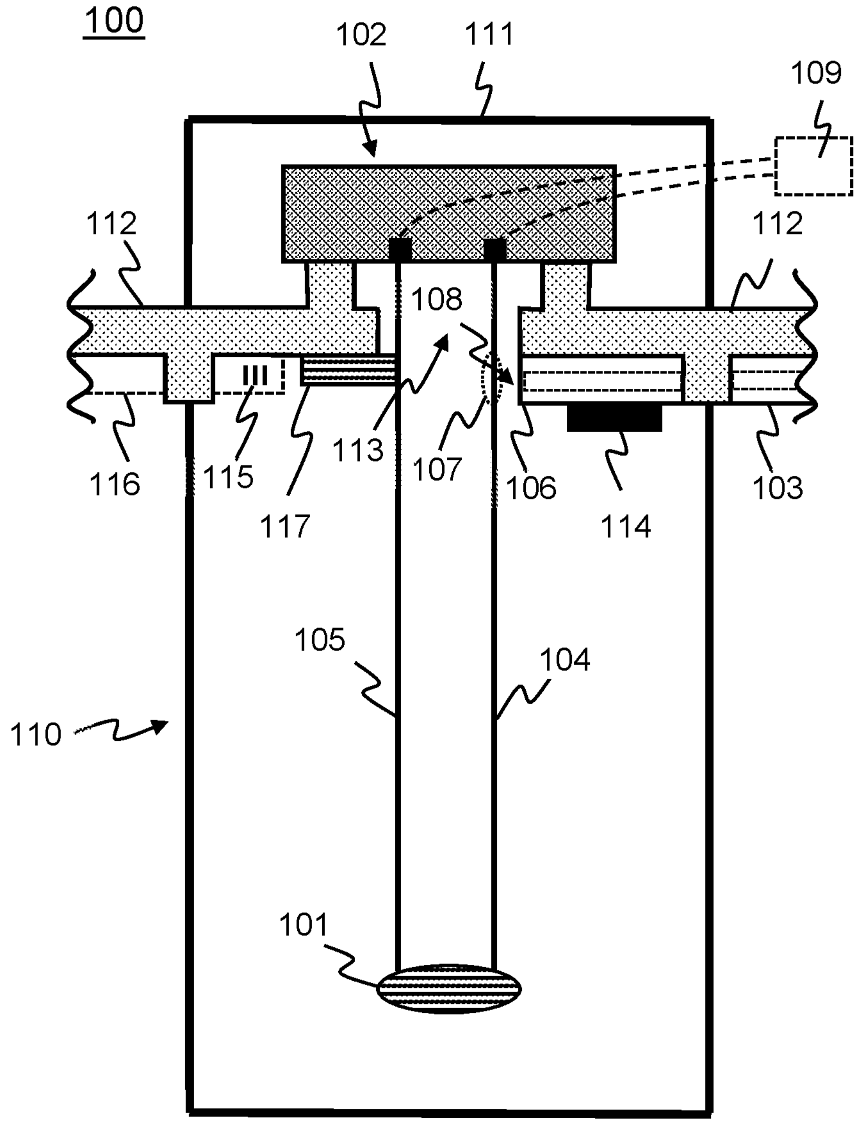
FIG. 1 is a schematic cross-sectional diagram of an optical measurement assembly for measuring a functional property of a biological tissue.

FIG. 1 schematically illustrates an optical measurement assembly 100 for measuring a functional property of a biological tissue 101. FIG. 1 provides a schematic cross-sectional diagram of the optical measurement assembly 100. The optical measurement assembly 100 illustrated in FIG. 1 is an embodiment that is compatible with standard laboratory equipment for growing and studying biological tissues. This will be apparent from the following description.

The optical measurement assembly 100 comprises a tissue suspension device 102 and an optical waveguide 103. The tissue suspension device 102 has two cantilevers 104, 105 between which the biological tissue 101 is suspended. The optical waveguide 103 has an end 106 that faces a surface part 107 of one of the two cantilevers 104, 105. This cantilever 104 will be referred to hereinafter as the measurement cantilever 104 for the sake of convenience, whereas the other cantilever 105 will be referred to as the complementary cantilever 105. The surface part 107 of the measurement cantilever 104 that faces the optical waveguide 103 is optically reflective.

The end 106 of the optical waveguide 103 and the surface part 107 of the measurement cantilever 104 that faces the end 106 of the optical waveguide 103 form an interferometric cavity 108. In this embodiment, the interferometric cavity 108 is a Fabry Perot cavity. The surface part 107 of the measurement cantilever 104 that forms, together with the optical waveguide 103, the interferometric cavity 108 will be referred to hereinafter as the interferometric surface part 107 for the sake of convenience.

The biological tissue 101 may be, for example, engineered heart or skeletal muscle tissues that are differentiated from induced pluripotent stem cells. As another example, the biological tissue 101 may originate from a biopsy. The biological tissue 101 may be in the form of, for example, a tissue bundle that has a length in the order of millimeters and a width that is somewhat smaller comprised in a range between, for example, 0.5 and 2 mm.

The measurement cantilever 104 may have a length in the order of tens of millimeters and a width in the order of millimeters. For example, the length of the measurement cantilever 104 may be in a range between 10 and 35 mm; the width of the measurement cantilever 104 may be in a range between 0.3 and 1.5 mm. The aforementioned may also apply to the complementary cantilever 105. The measurement cantilever 104 may have a thickness in the order of tens of micrometers to hundreds of micrometers. For example, the thickness of the measurement cantilever 104 may be in a range between 50 μm and 500 μm. The complementary cantilever 105 may have a similar thickness. The complementary cantilever 105 may also be thinner than the measurement cantilever 104 so that the measurement cantilever 104 is relatively flexible, whereas the complementary cantilever 105 is a relatively rigid. The measurement cantilever 104 may have a degree of compliance that is at least an order of magnitude greater than that of the complementary cantilever 105. This can contribute to reliable measurements, which will be explained hereinafter.

The two cantilevers 104, 105 may be electrically conductive. The two cantilevers 104, 105 may be electrically coupled to an electrical connector 109. Accordingly, in case an electrical stimulus is applied to the electrical connector 109, the biological tissue 101 that is suspended between the two cantilevers 104, 105 will be subject to the electrical stimulus. Thus, an electrical stimulus can be applied to the biological tissue 101 without this requiring specific electrodes in addition to the two cantilevers 104, 105. The electrical connector 109 need not form part of the optical measurement assembly 100 and is therefore illustrated in broken lines in FIG. 1. For example, the electrical connector 109 may be comprised in an entity that includes further optical measurement assemblies. Such a further optical measurement assembly may be similar to the optical measurement assembly 100 illustrated in FIG. 1 and may thus also comprise two cantilevers that are electrically conductive and coupled to the electrical connector 109.

In addition to being electrically conductive, the two cantilevers 104, 105 may be bio-inert so that these have no significant interaction with the biological tissue 101. Specifically, the two cantilevers 104, 105 may comprise metal, such as, for example, stainless steel, titanium, alumina, and partially stabilized zirconia. This provides advantages over conventional cantilevers made of polymer structures. Such conventional cantilevers can absorb small molecules, which may make that these can be used only once. Moreover, this can also reduce their effectiveness in analyzing biological tissues, which may concern, for example, drug screening.

The optical waveguide 103 may be in the form of, for example, an optical fiber. The optical waveguide 103 will be referred to hereinafter as optical fiber 103 for the sake of convenience and illustration. The optical fiber 103 may be in the form of, for example, a single-mode fiber optic cable that has been cleaved and aligned with the measurement cantilever 104. The end of the optical fiber 103 may be positioned with respect to the interferometric surface part 107 of the measurement cantilever 104 at a distance comprised in a range between, for example, 0.1 mm and 3 mm.

In this embodiment, the optical measurement assembly 100 further comprises a culture well 110. The culture well 110 may form part of a well plate comprising multiple culture wells. This will be discussed hereinafter. The two cantilevers 104, 105 between which the biological tissue 101 is suspended hang into the culture well 110. The optical measurement assembly 100 may further comprise a cover 111 for closing off the culture well 110 containing the biological tissue 101.

In this embodiment, the optical measurement assembly 100 comprises a support member 112 to which the optical fiber 103 is coupled. The optical fiber 103 is coupled to the support member 112 so that the end of the optical fiber 103 faces an opening 113 in the support member 112. The end of the optical fiber 103 is at a certain distance from a center in the opening 113. The optical fiber 103 may be secured to the support member 112 near the opening 113 by means of a ferrule 114. This mounting may define how the end of the optical fiber 103 is positioned with respect to the opening 113 and thus the distance with respect to the center of the opening 113.

The tissue suspension device 102 has been placed on the support member 112. The two cantilevers 104, 105 pass through the opening 113 in the support member 112. The tissue suspension device 102 rests on the support member 112 whereby the end of the optical fiber 103 faces the interferometric surface part 107 of the measurement cantilever 104. Another end of the optical fiber 103 may be coupled to, for example, an optical component that allows forming an optical path between the interferometric cavity 108 and an optical interrogator. This will be discussed hereinafter in greater detail.

The support member 112 may be in the form of, for example, a relatively thin plate. The support member 112 will be referred to hereinafter as fiber routing plate 112 for the sake of convenience and illustration. In this embodiment, the fiber routing plate 112 has been placed on the culture well 110. The opening 113 in the fiber routing plate 112 opens into the culture well 110. The fiber routing plate 112 may extend over further culture wells that form part of the same well plate as the culture well 110 illustrated in FIG. 1. In such an embodiment, further optical fibers may be coupled to the fiber routing plate 112, where such a further optical fiber 103 may be uniquely associated with a further culture well 110. This will be described in greater detail hereinafter.

The optical measurement assembly 100 may comprise at least one fiber optic sensor 115 for measuring at least one parameter of an environmental condition to which the biological tissue 101 is exposed. FIG. 1 schematically represents only one such fiber optic sensor 115 for the sake of simplicity. The fiber optic sensor 115 may measure, for example, a concentration of calcium (Ca), or of oxygen ($O_2$), or of nitrogen ($N_2$), or of carbon dioxide ($CO_2$) in the culture well 110, or may measure any combination of these. As another example, the fiber optic sensor 115 may measure a pH in the culture well 110. The fiber optic sensor 115 may be coupled to, or form part of, an additional optical fiber 116 that is associated with the culture well 110. This additional optical fiber 116 may also be coupled to the fiber routing plate 112. An end of the additional optical fiber 116, which is opposite to the fiber optic sensor 115, may be coupled to an optical component that allows forming an optical path between the fiber optic sensor 115 and an optical interrogator. This optical interrogator may be the same as the one mentioned hereinbefore with respect to the interferometric cavity 108.

The optical measurement assembly 100 may comprise at least one actuator 117 that is operatively coupled to at least one of the two cantilevers 104, 105. FIG. 1 schematically represents only one actuator 117 for the sake of simplicity. This actuator 117 is operatively coupled to the complementary cantilever 105 by way of illustration. The actuator 117 may cause a displacement of the complementary cantilever 105. As a result, a force can be exerted on the biological tissue 101 that is suspended between the two cantilevers 104, 105. Alternatively, or complementary, an actuator 117 may be operatively coupled to the measurement cantilever 104 for this purpose. The actuator 117 may be in the form of, for example, a piezo-electrical device, an electro-magnetic device, which may include a coil, or another type of actuator 117.

The optical measurement assembly 100 basically operates as follows. The biological tissue 101 may beat, or contract or expand, or both. In each of these cases, the biological tissue 101 then exerts a force on the two cantilevers 104, 105. This will cause the measurement cantilever 104 to flex to a degree that depends on the force that the biological tissue 101 exerts and on a degree of elasticity of the measurement cantilever 104. The biological tissue 101 may beat, or contract or expand either spontaneously or in response to an electrical stimulus. As indicated hereinbefore, the electrical stimulus may be applied to the electrical connector 109 illustrated in FIG. 1. The electrical stimulus will then reach the biological tissue 101 through the two cantilevers 104, 105, which are electrically conductive. The electrical stimulus may be in the form of, for example, electrical pacing.

The interferometric cavity 108 has a spectral response that depends on an optical path length within the interferometric cavity 108. The optical path length is defined by two factors. One factor is a distance between the end of the optical fiber 103 and the interferometric surface part 107 of the measurement cantilever 104. This distance will be referred to hereinafter as the interferometric cavity length for the sake of convenience. The other factor that defines the optical path length is a refractive index of a medium that exists between the aforementioned two entities that form the interferometric cavity 108. The latter factor may be regarded as constant.

Measuring a change in the spectral response allows measuring the force that the biological tissue 101 exerts on the measurement cantilever 104 with relatively great precision. In case the measurement cantilever 104 flexes, the optical path length within the interferometric cavity 108 changes and, consequently, the spectral response changes. A change in the interferometric cavity length can be quantitively determined with relatively great precision on the basis of a change in the spectral response that is measured. The force that the biological tissue 101 exerts can be calculated on the basis of the change in the interferometric cavity length and several known factors that concern the measurement cantilever 104. These known factors include the degree of elasticity of the measurement cantilever 104 and a geometric relationship between a point where the biological tissue 101 is attached to the measurement cantilever 104 with respect to where the interferometric surface part 107 is located on the measurement cantilever 104.

The actuator 117 may be used to exercise, as it were, the biological tissue 101 prior to measuring the force that the biological tissue 101 generates in response to an electrical stimulus, or in between such measurements. In an embodiment comprising multiple optical measurement assemblies similar to that illustrated in FIG. 1, the actuator 117 may enable many tensile test measurements in parallel. The fiber optic sensor 115 allows obtaining information on the environmental condition to which the biological tissue 101 is exposed. As discussed hereinbefore, this information may concern measured concentrations of one or more substances, or the pH, or any combination of these and other parameters.

The optical measurement assembly 100 illustrated in FIG. 1 provides various advantages. A force exerted by the biological tissue 101 can be measured with relatively great precision. The optical measurement assembly 100 can thus reliably measure a relatively weak force exerted by the biological tissue 101. That is, the optical measurement assembly 100 allows sensitive measurements. The optical measurement assembly 100 may be several orders of magnitude more sensitive than conventional devices for measuring a force exerted by a biological tissue 101 suspended between two cantilevers 104, 105. Accordingly, the optical measurement assembly 100 allows for experiments on less mature biological tissues, which are weaker. As a result, the optical measurement assembly 100 may improve throughput in laboratories and other environments where experiments may be conducted. Sensitive measurements may also provide more information on the biological tissue 101 responding to a relatively small changes or differences in environmental conditions.

The information on the force that the biological tissue 101 exerts is carried by an optical signal. The information on the environmental condition to which the biological tissue 101 is exposed, if acquired, is also carried by an optical signal. All this information is transferred through optical fibers in an inherently synchronous manner. Moreover, a single optical interrogator may retrieve and process all this information. Accordingly, a relatively high time resolution can be achieved. A change in the force that the biological tissue 101 exerts can be related to a change in the environmental condition, and vice versa, with a relatively great precision.

The optical measurement assembly 100 further allows measuring an electrical characteristic of the biological tissue 101 through the two cantilevers 104, 105 that are electrically conductive. The electrical characteristic may be measured, for example, in applying electrical stimulus to the biological tissue 101. The electrical characteristic may be for example, an impedance, an admittance, a resistance, or a conductance of the biological tissue 101. The electrical characteristic may provide information on the biological tissue 101. This information may relate to, for example, size of the biological tissue 101, or composition of the biological tissue 101, or a combination of these, as well as other types of information.

The optical measurement assembly 100 illustrated in FIG. 1 may be used, for example, in research aiming at assessing efficacy and toxicity of drugs, which may also involve making disease models. For example, an effect of a drug on arrythmias can be assessed with a high degree of fidelity. The aforementioned sensitivity and precision of the measurement assembly contributes to this, as well as the biological tissue 101 being three-dimensional rather than a flat strip of tissue. Use of the optical measurement assembly 100 may thus improve a drug development process by more faithfully and precisely assessing a response of to a drug compared with conventional techniques.

As another example, the optical measurement assembly 100 may be used in research towards regenerative medicine. The optical measurement assembly 100 allows precisely monitoring a degree of maturity of stem cells. The optical measurement assembly 100 allows assessing quality and health of the biological tissue 101 in a relatively fast and nondestructive manner. The optical measurement assembly 100 can thus provide a platform improving maturation.

Figure 2:
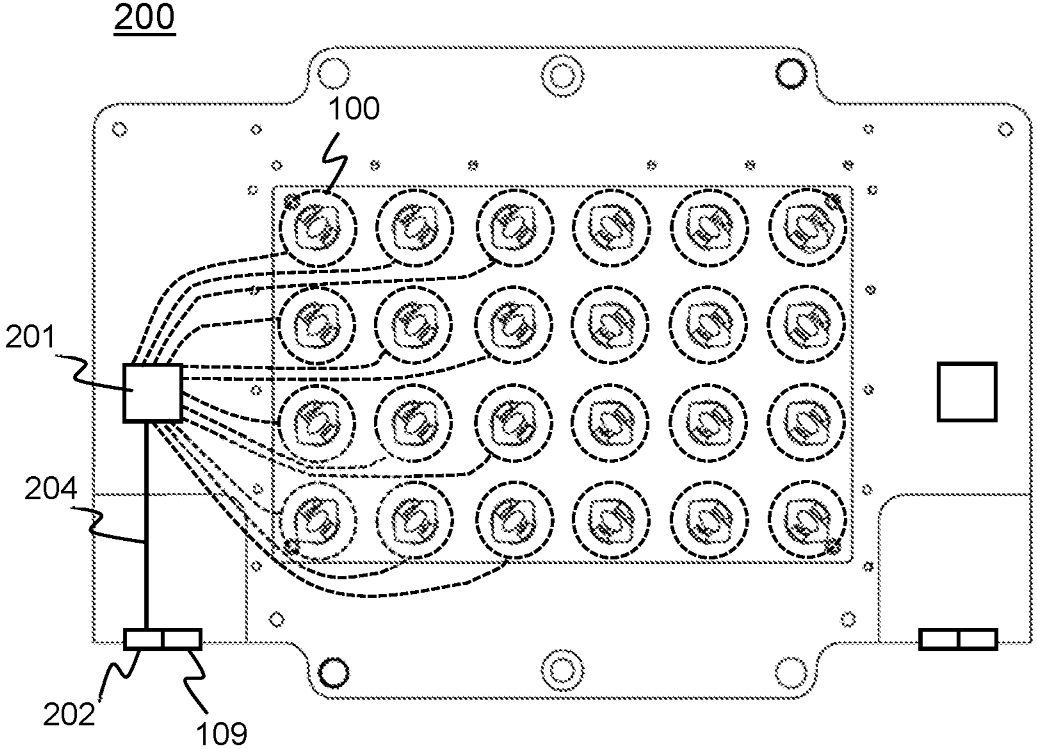
FIG. 2 is a schematic top view of a complex of optical measurement assemblies, which may each be similar to the optical measurement assembly illustrated in FIG. 1.

FIG. 2 schematically illustrates a complex of optical measurement assemblies 200. FIG. 2 provides a schematic top view of the complex of optical measurement assemblies 200. The optical measurement assemblies schematically are indicated as circles in broken lines. An upper left optical measurement assembly is indicated as corresponding with the optical measurement assembly 100 described hereinbefore with reference to FIG. 1. All the other optical measurement assemblies may also each correspond with the optical measurement assembly 100 illustrated in FIG. 1. For the sake of explanation, it is assumed that this is the case. The tissue suspension device of each optical measurement assembly is schematically depicted within the circle indicating the optical measurement assembly concerned. The culture well of each optical measurement assembly may form part of a well plate. In this embodiment, the well plate comprises 24 culture wells. In other embodiments, the complex of optical measurement assemblies 200 may be based on a well plate that comprises a smaller or a greater number of culture wells, such as, for example 96 culture wells.

The complex of optical measurement assemblies 200 may comprise a fiber splitter 201, an optical connector 202 and the electrical connector 109 mentioned hereinbefore, which is also schematically represented in FIG. 1. FIG. 2 illustrates an embodiment in which there are two groups of optical measurement assemblies, a left-hand group and a right hand group, each having their own fiber splitter 201, optical connector 202 and electrical connector 109. In the left-hand group, several optical fibers from several interferometric cavities are jointly coupled to the fiber splitter 201 of this group. These optical fibers are schematically depicted in broken lines. The fiber splitter 201 may be coupled to the optical connector 202 through a further optical fiber 204. Similarly, several pairs of cantilevers of several optical measurement assemblies may jointly be electrically connected to the electrical connector 109. These electrical connections are not represented in FIG. 2 for the sake of simplicity. The aforementioned equally applied to the right-hand group of optical measurement assemblies. Optical fiber connections between these optical measurement assemblies and the fiber splitter 201 of this group are not represented in FIG. 2 for the sake of simplicity.

The spectral response of the interferometric cavity in each optical measurement assembly may be different from that of the interferometric cavity in each of the other optical measurement assemblies. That is, spectral responses are each unique and therefore distinguishable from each other. For example, each spectral response may exhibit a unique periodicity. This may be achieved, for example, by making that each optical measurement assembly has a different interferometric cavity length.

Figure 3:
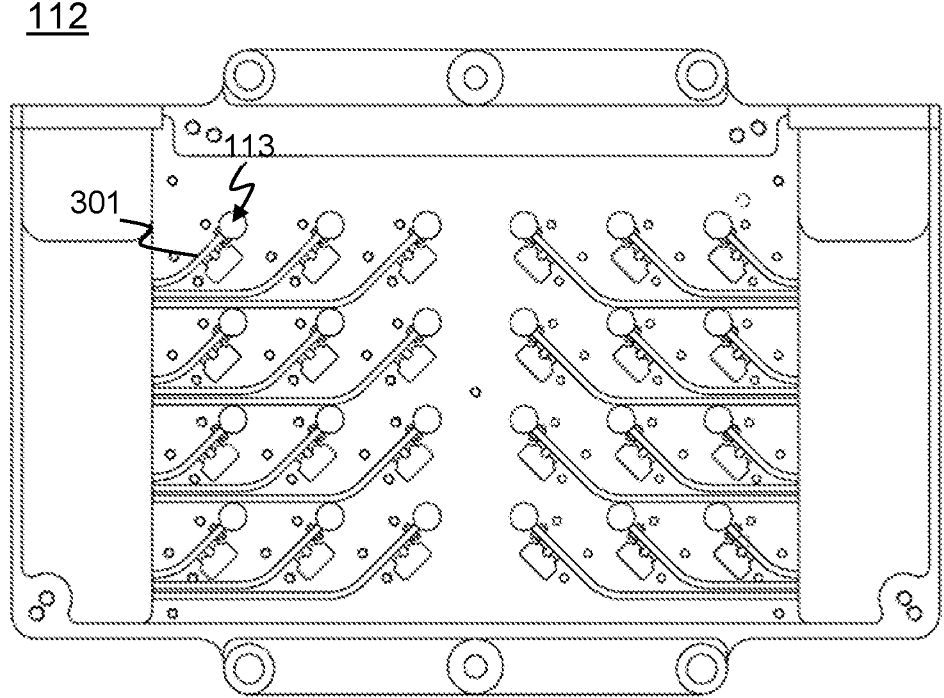
FIG. 3 is a schematic bottom view of a support member, which may form part of the complex of optical measurement assemblies.

FIG. 3 schematically illustrates an embodiment of the fiber routing plate 112 mentioned hereinbefore. FIG. 3 provides a schematic bottom view of the fiber routing plate 112. The fiber routing plate 112 may form part of the complex of optical measurement assemblies 200 illustrated in FIG. 2. For the sake of explanation, it is assumed that this is the case.

The fiber routing plate 112 comprises a number of openings that corresponds with that of the optical measurement assemblies in the complex illustrated in FIG. 2. An opening lies uniquely within an optical measurement assembly. That is, each optical measurement assembly has its own opening. The opening thus opens into the culture well that forms part of the same optical measurement assembly. An upper left opening 113 is indicated as corresponding with the opening 113 of the optical measurement assembly 100 described hereinbefore with reference to FIG. 1.

In this embodiment, the fiber routing plate 112 comprises multiple trenches for guiding multiple optical fibers. An upper left trench 301 guides the optical fiber 103 of the optical measurement assembly 100 described hereinbefore with reference to FIG. 1. In general, a trench uniquely guides an optical fiber to an opening and thus to the optical measurement assembly in which the opening lies. The end of the optical fiber may be positioned with respect to the opening in a unique manner. That is, for each opening, the distance between the end of the optical fiber and the center of the opening may be unique. Accordingly, the interferometric cavity length of each optical measurement assembly may be unique. As a result, the spectral response of each interferometric cavity may be unique. Each spectral response may have a periodicity that is different from the periodicity in the spectral response of each of the other interferometric cavities.

Figure 4:
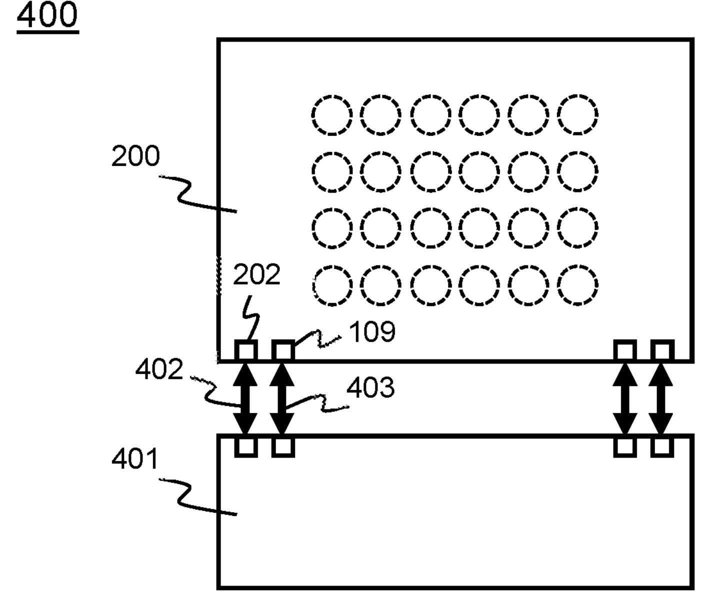
FIG. 4 is a schematic block diagram of an optical measurement system, which may comprise the complex of optical measurement assemblies illustrated in FIG. 2.

FIG. 4 schematically illustrates of an optical measurement system 400. FIG. 4 provides a schematic block diagram of the optical measurement system 400. In this embodiment, the optical measurement system 400 comprises the complex of optical measurement assemblies 200 illustrated in FIG. 2. The optical measurement system 400 further comprises an optical interrogator 401.

An optical connection 402 optically couples the complex of optical measurement assemblies 200 to the optical interrogator 401. The optical connection 402 has an end that engages with the optical connector 202 of the complex of optical measurement assemblies 200. Another end of the optical connection 402 engages with an optical connector of the optical interrogator 401. The optical interrogator 401 is thus optically coupled to multiple interferometric cavities in multiple optical measurement assemblies, namely in those that belong to the left-hand group mentioned hereinbefore with reference to FIG. 2. This parallel optical coupling is achieved through the fiber splitter 201 illustrated in FIG. 2.

Likewise, an electrical connection 403 electrically couples the complex of optical measurement assemblies 200 to the optical interrogator 401. The electrical connection 403 has an end that engages with the electrical connector 109 of the complex of measurement assemblies. Another end of the electrical connection 403 engages with an electrical connector of the optical interrogator 401. The optical interrogator 401 is thus electrically coupled to multiple pairs of cantilevers in multiple optical measurement assemblies, namely in those that belong to the left-hand group mentioned hereinbefore with reference to FIG. 2.

The optical measurement system 400 basically operates as follows. The optical interrogator 401 injects light into the complex of optical measurement assemblies 200 through the optical connector 202 thereof. This injected light reaches the interferometric cavities that are coupled to the optical connector 202 through the fiber splitter 201 illustrated in FIG. 2. In response, the optical interrogator 401 receives reflected light, which is a combination of light reflected by each of the interferometric cavities.

The reflected light that the optical interrogator 401 receives has a spectrum that is a combination the respective spectral responses of the respective interferometric cavities receiving the injected light. The optical interrogator 401 may analyze a spectral response so as to obtain information on a biological tissue in the optical measurement assembly comprising the interferometric cavity that provides the spectral response. The interferometric cavity, and thus the measurement assembly, can be identified on the basis of a parameter that differentiates the spectral response from the other spectral responses. This parameter may be, for example, the periodicity in the spectral response, as discussed hereinbefore.

The optical interrogator 401 may analyze various spectral responses in parallel, that is, simultaneously. This is a fast, time efficient approach for obtaining information on various biological tissues that have been placed in the complex of optical measurement assemblies 200. For example, respective forces that respective biological tissues exert on respective measurement cantilevers in the respective optical measurement assemblies can simultaneously be measured. As explained hereinbefore with reference to FIG. 1, the optical interrogator 401 may calculate such a force based on a measured change in the spectral response of the interferometric cavity 108 in the optical measurement assembly 100. These measurements can thus be done simultaneously, in parallel, which may extend to, for example, 96 culture wells on a culture plate. Moreover, as mentioned hereinbefore, these measurements provide a degree of precision and sensitivity that may be orders of magnitude higher than that achievable with prior art techniques.

The optical interrogator 401 may operate in a manner similar to that described in patent publication WO2017077138A1. This allows carrying out relatively precise measurements of changes in spectral responses and doing so simultaneously, in parallel. In a nutshell, the manner of operation described in WO2017077138A1 involves repetitively measuring the spectrum of the reflected light received by the optical interrogator 401. A Fourier-like transform is applied to the spectrum so as to obtain a Fourier-like transformed spectrum. The Fourier-like transform may be complex so that an amplitude representation of the Fourier-like transformed spectrum is obtained, as well as a phase representation of the Fourier-like transformed spectrum. The amplitude representation exhibits respective peaks at respective locations. A location where a peak occurs uniquely corresponds with the periodicity of the spectral response of an interferometric cavity. The location in the Fourier-like transformed spectrum thus uniquely identifies the interferometric cavity. A phase evolution in successive phase representations around the location provides a relatively precise representation of a change in the spectral response of the interferometric cavity.

The optical interrogator 401 may apply an electrical stimulus to the complex of optical measurement assemblies 200 through the electrical connector 109 thereof. The electrical stimulus may reach multiple pairs of cantilevers in multiple optical measurement assemblies that are coupled to the electrical connector 109. Biological tissues that are suspended between these multiple pairs of cantilevers thus receive the electrical stimulus. In response, the biological tissues may, for example, contract. The optical interrogator 401 may measure respective forces that respective biological tissues exert due to their contraction. This measurement can be carried out as described hereinbefore. In addition, the optical interrogator 401 may carry out an electrical measurement by means of an electrical signal applied to the electrical connector 109, which may be, for example, the electrical stimulus. As described with reference to FIG. 1, the electrical measurement allows obtaining additional information on the biological tissues that are present in the complex of optical measurement assemblies 200.

Figures 5, 6, 7:
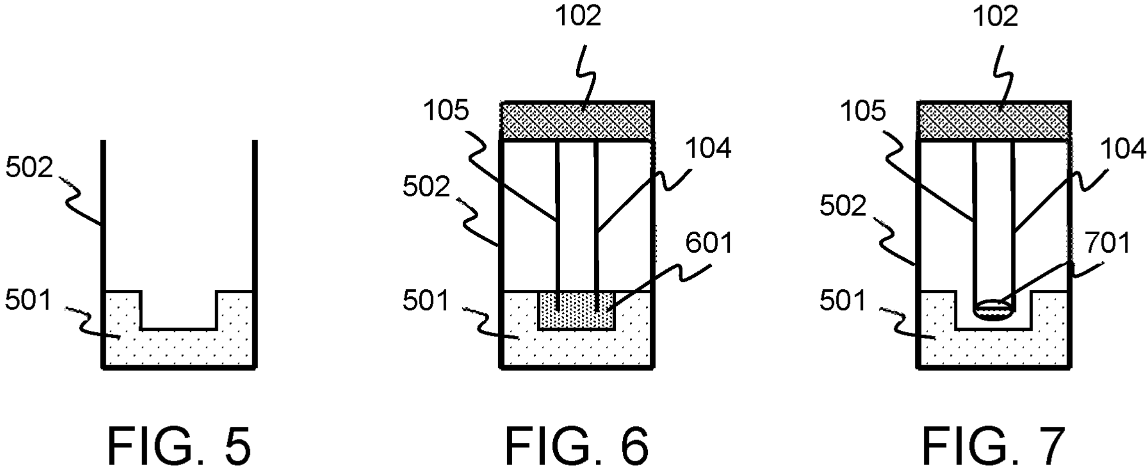
FIG. 5 is a schematic cross-sectional diagram of entities involved at an initial stage of a process to obtain the biological tissue suspended between two cantilevers of a tissue suspension device.
FIG. 6 is a schematic cross-sectional diagram of entities involved at a pre-incubation stage of the aforementioned process.
FIG. 7 is a schematic cross-sectional diagram of entities involved at a post-incubation stage of the aforementioned process.

FIGS. 5-7 schematically illustrate various stages in a process to obtain the biological tissue 101 suspended between the two cantilevers 104, 105 of the tissue suspension device 102 as illustrated in FIG. 1. FIGS. 5-7 each provide a schematic cross-sectional diagram of entities that are involved at the stage concerned.

FIG. 5 schematically illustrates an initial stage of the aforementioned process. At this stage, a bed of agarose gel 501, or another suitable substance, has been provided on a bottom of an initial culture well 502. The initial culture well 502 may be similar to the culture well 110 of the optical measurement assembly 100 that has been described hereinbefore with reference to FIG. 1. Accordingly, the initial culture well 502 may equally form part of an initial well plate comprising multiple initial culture wells.

FIG. 6 schematically illustrates pre-incubation stage of the aforementioned process. At this stage, a mixture 601 comprising tissue cells and an extracellular matrix has been cast in the bed of agarose gel 501 by means of, for example, pipetting. The extracellular matrix may comprise, for example, a hydrogel. The tissue suspension device 102 has been placed on top of the initial culture well 502, whereby the tissue suspension device 102 may constitute a lid that covers the initial culture well 502, at least partially. Tip portions of the two cantilevers 104, 105 of the tissue suspension device 102 protrude into the mixture 601 that comprises the tissue cells. The initial culture well 502 that now contains the mixture 601 comprising tissue cells and on which the tissue suspension device 102 has been placed, as illustrated in FIG. 7, may be placed in an incubator.

FIG. 7 schematically illustrates a post-incubation stage of the aforementioned process. The post-incubation stage may be reached after a suitable incubation period in the incubator, which may be, for example, a few days. The aforementioned mixture 601 comprising the extracellular matrix has compacted and has detached from the bed of agarose gel 501. A premature biological tissue 701 has formed and may be fixedly suspended between the two cantilevers 104, 105. The tissue suspension device 102 may now be removed from the initial culture well 502 and placed on a new culture well, which may be the culture well 110 of the optical measurement assembly 100 illustrated in FIG. 1. Culturing may continue until, for example, the premature biological tissue 701 matures and becomes sufficiently contractile to form the biological tissue 101 illustrated in FIG. 1. This may take, for example, about 9 days. The biological tissue 101 being sufficiently contractile is then ready to undergo measurements as described hereinbefore.

The embodiments described hereinbefore with reference to the drawings are presented by way of illustration. The invention may be implemented in numerous different ways. In order to illustrate this, some alternatives are briefly indicated.

The invention may be applied in numerous types of products or methods related to optically measuring a functional property of a tissue. In the presented embodiments, a contractile force is measured. In other embodiments, a stiffness of the tissue, for example, may be measured.

There are numerous different ways of implementing an optical measurement assembly in accordance with the invention. In the embodiments presented hereinbefore, a single interferometric cavity is formed by an end of an optical waveguide facing a reflective surface part of one of two cantilevers. In other embodiments, two such interferometric cavities may be formed, one involving one of two cantilevers, the other interferometric cavity involving the other of the two cantilevers. For example, such an alternative embodiment may be obtained by making the following modifications to the embodiment illustrated in FIG. 1. A further optical waveguide is provided having an end that faces a surface part of the complementary cantilever 105. This surface part of the complementary cantilever 105 optically reflective too so that a further interferometric cavity is formed with the further optical waveguide. This further interferometric cavity then has a spectral response that varies as a function of a degree of flexion of the complementary cantilever.

In the embodiments presented hereinbefore, the tissue suspension device is received in a support member having an opening through which the two cantilevers pass. The optical waveguide is coupled to the support member so that its end faces this opening. In other embodiments, the suspension device and the optical waveguide may be in relation with each other by different means. For example, a coupling member may be provided for coupling the suspension device and the optical waveguide with each other. Such a coupling member may be in the form of, for example, a clip or a clamp, and the like, present on a base of the suspension device from which the two cantilevers extend.

There are numerous different ways of implementing an optical interferometric cavity in an optical measurement assembly in accordance with the invention. In the embodiments presented hereinbefore, the optical interferometric cavity is a Fabry-Perot cavity. In other embodiments, the optical interferometric cavity may be, for example, a Michelson cavity.

There are numerous different ways of implementing an optical waveguide in an optical measurement assembly in accordance with the invention. In the embodiments presented hereinbefore, the optical waveguide is an optical fiber. In other embodiments, the optical waveguide may be comprised in an integrated photonics system. The integrated photonic systems may be implemented on a substrate, which may constitute a support member similar to the support member 112 in the embodiments presented hereinbefore.

There are numerous different ways of measuring the spectral response of the optical interferometric cavity in an optical measurement assembly in accordance with the invention. In the embodiments presented hereinbefore, an optical interrogator is used that operates in accordance with a technique as described in WO2017077138A1, which allows precise measurements that can be carried out in parallel. In other embodiments, the spectral response may be measured using a technique different from that described in the aforementioned patent publication.

The remarks made hereinbefore demonstrate that the embodiments described with reference to the drawings illustrate the invention, rather than limit the invention. The invention can be implemented in numerous alternative ways that are within the scope of the appended claims. All changes that come within the meaning and range of equivalency of the claims are to be embraced within their scope. Any reference sign in a claim should not be construed as limiting the claim. The verb "comprise" in a claim does not exclude the presence of other elements or other steps than those listed in the claim. The same applies to similar verbs such as "include" and "contain". The mention of an element in singular in a claim pertaining to a product, does not exclude that the product may comprise a plurality of such elements. Likewise, the mention of a step in singular in a claim pertaining to a method does not exclude that the method may comprise a plurality of such steps. The mere fact that respective dependent claims define respective additional features, does not exclude combinations of additional features other than those reflected in the claims.

The invention claimed is:

1. An optical measurement assembly comprising:

a tissue suspension device having two cantilevers between which a biological tissue can be suspended; and an optical waveguide having an end that faces a surface part of one of the two cantilevers, the surface part being optically reflective so that the optical waveguide and the surface part form an interferometric cavity having a spectral response that varies as a function of a degree of flexion of the cantilever of which the surface part faces the optical waveguide.

2. An optical measurement assembly according to claim 1 comprising:

a support member to which the optical waveguide is coupled so that the end of the optical waveguide faces an opening in the support member, the support member being adapted to receive the tissue suspension device such that the two cantilevers pass through the opening in the support member and the tissue suspension device rests on the support member, whereby the end of the optical waveguide faces the surface part of the one of the two cantilevers.

3. An optical measurement assembly according to claim 1, wherein the end of the optical waveguide is positioned with respect to the surface part of the cantilever at a distance comprised in a range between 0.1 mm and 3 mm.

4. An optical measurement assembly according to claim 1, wherein the cantilever of which the surface part faces the end of the optical waveguide has:

a length in a range between 1 mm and 35 mm;

a width in a range between 0.3 mm and 1.5 mm; and a thickness in a range between 0.05 mm and 0.5 mm.

5. An optical measurement assembly according to claim 1, wherein the cantilever of which the surface part faces the end of the optical waveguide has a degree of compliance that is at least an order of magnitude greater than that of the other cantilever.

6. An optical measurement assembly according to claim 1, wherein the two cantilevers are electrically conductive and electrically coupled to an electrical connector adapted to receive an electrical stimulus to be applied to the biological tissue suspended between the two cantilevers.

7. An optical measurement assembly according to claim 1, comprising at least one actuator operatively coupled to at least one of the two cantilevers so as to exert a force on the biological tissue suspended between the two cantilevers.

8. An optical measurement assembly according to claim 1, comprising at least one optical sensor for measuring at least one parameter of an environmental condition to which the biological tissue is exposed.

9. An optical measurement assembly according to claim 1, comprising a further optical waveguide having an end that faces a surface part of the other cantilever, the surface part of the other cantilever being optically reflective so that the further optical waveguide and the surface part of the other cantilever form a further interferometric cavity having spectral response that varies as a function of a degree of flexion of the other cantilever.

10. A complex of optical measurement assemblies according to claim 1, wherein respective interferometric cavities have respective spectral responses that are different from each other.

11. A complex according to claim 10 comprising a splitter that is coupled, on one hand, to respective optical waveguides of respective optical measurement assemblies and, on the other hand, to an optical connector adapted to be coupled to an optical interrogator.

12. An optical measurement system comprising an optical measurement assembly according to claim 1, and an optical interrogator adapted to measure a change in the spectral response of the interferometric cavity formed by the end of the optical waveguide and the surface part of the cantilever that faces the end of the optical waveguide.

13. An optical measurement system according to claim 12, the optical measurement system being adapted to calculate a force exerted by the biological tissue based on the change in the spectral response of the interferometric cavity.

14. An optical measurement system according to claim 12, the optical measurement system being adapted to apply an electrical stimulus to the biological tissue suspended between the two cantilevers.

15. A method of optically measuring at least one functional property of a biological tissue, the method comprising:

providing a biological tissue that is suspended between two cantilevers of a tissue suspension device;

positioning the tissue suspension device with respect to an end of an optical waveguide so that the end of the optical waveguide faces a surface part of one of the two cantilevers, the surface part being optically reflective so that the end of the optical waveguide and the surface part form an interferometric cavity having a spectral response that varies as a function of a degree of flexion of the cantilever of which the surface part faces the optical waveguide;

measuring a change in the spectral response of the interferometric cavity; and calculating a force exerted by the biological tissue from the change in the spectral response of the interferometric cavity, the force being representative of a functional property of the biological tissue.

16. A method according to claim 15, the method comprising:

applying a stimulus to the biological tissue whereby the change in the spectral response of the interferometric cavity is measured as a response to the stimulus.

17. A method according to claim 16, wherein positioning the tissue suspension device with respect to the end of the optical waveguide comprises:

using a support member to which the optical waveguide is coupled so that the end of the optical waveguide faces an opening in the support member; and placing the tissue suspension device on the support member so that the two cantilevers pass through the opening in the support member whereby the end of the optical waveguide faces the surface part of the one of the two cantilevers.

18. A method according to claim 17, the method comprising prior to placing the tissue suspension device on the support member:

placing the support member on a culture well so that the two cantilevers hang into the culture well when these have been passed through the opening in the support member.

19. A method according to claim 15, wherein providing the biological tissue comprises:

providing the two cantilevers of the tissue suspension device with a mixture containing cells; and incubating the tissue suspension device with the mixture containing cells so that the biological tissue is formed from the mixture.

* * * * *